US012399563B2

(12) United States Patent
Chin et al.

(10) Patent No.: US 12,399,563 B2
(45) Date of Patent: Aug. 26, 2025

(54) CLASSIFYING SIGNALS FOR MOVEMENT CONTROL OF AN AUTONOMOUS VEHICLE

(71) Applicant: AGENCY FOR SCIENCE, TECHNOLOGY AND RESEARCH, Singapore (SG)

(72) Inventors: Zheng Yang Chin, Singapore (SG); Kai Keng Ang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1002 days.

(21) Appl. No.: 17/599,099

(22) PCT Filed: Mar. 29, 2019

(86) PCT No.: PCT/SG2019/050181
§ 371 (c)(1),
(2) Date: Sep. 28, 2021

(87) PCT Pub. No.: WO2020/204809
PCT Pub. Date: Oct. 8, 2020

(65) Prior Publication Data
US 2022/0164029 A1    May 26, 2022

(51) Int. Cl.
*G06F 3/01* (2006.01)
*G06F 18/21* (2023.01)
(Continued)

(52) U.S. Cl.
CPC .............. *G06F 3/015* (2013.01); *G06F 3/017* (2013.01); *G06F 18/2193* (2023.01);
(Continued)

(58) Field of Classification Search
CPC ..... G06N 20/00; G06F 18/22; G06F 18/2193; G06F 18/23; G06F 3/015; G06F 3/017
See application file for complete search history.

(56) References Cited

U.S. PATENT DOCUMENTS 6,070,098 A * 5/2000 Moore-Ede .......... A61B 5/7267
600/300
2012/0179008 A1  7/2012 Burton
(Continued)

FOREIGN PATENT DOCUMENTS

CN    106963372 A    7/2017
CN    107357311 A    11/2017

OTHER PUBLICATIONS

Rechy-Ramirez E. J. et al., Bio-signal based control in assistive robots: a survey, *Digital Communications and Networks*, Mar. 17, 2015, vol. 1, pp. 85-101 [Retrieved on Jun. 18, 2019] <DOI: http://dx.doi.org/10.1016/j.dcan.2015.02.004> Figs. 1-4; Table 5; pp. 86-88, 93-96.
(Continued)

*Primary Examiner* — Tadesse Hailu
(74) *Attorney, Agent, or Firm* — HARNESS, DICKEY & PIERCE, P.L.C.

(57) ABSTRACT

Disclosed is a method for classifying signals for movement control of an autonomous vehicle. The method includes receiving first data comprising concurrently recorded electroencephalogram (EEG) and electromyogram (EMG) signals from a user. The data is used to train a classification model based on the recorded signals. The method further involves receiving second data comprising further EEG and EMG signals recorded from the user, comparing the second data to the classification model to determine a user movement represented by the second data, and determining a control signal for controlling the autonomous vehicle, based on the user movement. This may be used in a further method for identifying an event.

20 Claims, 12 Drawing Sheets

(51) Int. Cl.
    *G06F 18/22*     (2023.01)
    *G06F 18/23*     (2023.01)
    *G06N 20/00*     (2019.01)

(52) U.S. Cl.
    CPC ............. *G06F 18/22* (2023.01); *G06F 18/23* (2023.01); *G06N 20/00* (2019.01)

(56) References Cited

U.S. PATENT DOCUMENTS

| | | | |
|---|---|---|---|
| 2019/0061772 A1* | 2/2019 | Prinz | B60K 28/06 |
| 2019/0332902 A1* | 10/2019 | Gallagher | G06V 10/811 |
| 2020/0337645 A1* | 10/2020 | Kremen | A61B 5/389 |

OTHER PUBLICATIONS

Hong K.-S. et al., Hybrid Brain-Computer interface Techniques for improved Classification Accuracy and increased Number of Commands: A Review, *Frontiers in Neurorobotics*, Jul. 24, 2017, vol. 11, No. 35, pp. 1-27 [Retrieved on Jun. 18, 2019] <DOI: 10.3389/FNBOT.2017.00035> Figs. 1, 2, 4; pp. 5-7, 10.

Lalitharatne T. D. et al, Towards Hybrid EEG-EMG-Based Control Approaches to be Used in Bio-robotics Applications: Current Status, Challenges and Future Directions, *Paladyn, Journal of Behavioral Robotics*, Dec. 10, 2013, vol. 4, No. 2, pp. 147-154 [Retrieved on Jun. 18, 2019] <DOI: 10.2478/PJBR-2013-0009 >Figs. 1-4; pp. 148-152.

Chowdhury A. et al., EEG-EMG based Hybrid Brain Computer Interface for Triggering Hand Exoskeleton for Neuro-Rehabilitation, *3rd International Conference of Robotics Society of India*, Nov. 23, 2017 [Retrieved on Jun. 18, 2019] <DOI: 10.1145/3132446.3134909> Figs. 1, 5-7; pp. 3-6.

Sarasola-Sanz A et al., A Hybrid Brain-Machine Interface based on EEG and EMG activity for the Motor Rehabilitation of Stroke Patients., Jul. 20, 2017, pp. 1-6 [Retrieved on Jun. 18, 2019] <DOI: 10.1109/ICORR.2017.8009362 > Fig. 1; p. 1-3.

Li X. et al., A motion-classification strategy based on sEMG-EEG signal combination for upperlimb amputees, *Journal of NeuroEngineering and Rehabilitation*, Jan. 7, 2017, vol. 14, No. 2, pp. 1-13 [Retrieved on Jun. 18, 2019] <DOI: 10.1186/S12984-016-0212-Z>Fig. 3; pp. 2-5.

Ferreira A. et al., Human-machine interfaces based on EMG and EEG applied to robotic systems, *Journal of NeuroEngineering and Rehabilitation*, Mar. 26, 2008, vol. 5, No. 10, pp. 1-15 [Retrieved on Jun. 18, 2019] <DOI: 10.1186/1743-0003-5-10> FIG. 1; pp. 2, 7.

International Search Report and Written Opinion of the ISA issued in PCT/SG2019/050181, mailed Jun. 18, 2019; ISA/SG.

\* cited by examiner

CLASSIFYING SIGNALS FOR MOVEMENT CONTROL OF AN AUTONOMOUS VEHICLE

CROSS-REFERENCE TO RELATED APPLICATIONS

This application is a U.S. National Phase Application under 35 U.S.C. 371 of International Application No. PCT/SG2019/050181, filed on Mar. 29, 2019. The entire disclosure of the above application is incorporated herein by reference.

TECHNICAL FIELD

The present invention relates, in general terms, to a system for classifying signals for movement control of an autonomous vehicle, to a system for identifying an event—e.g., an event represented in signals derived from corporeal electrical activity—and computer processes performed on those systems.

BACKGROUND

Recognition of the importance of using corporeal electrical activity—e.g., muscle or brain activity—for control of devices has been increasing in recent decades. In particular, the desire to provide control and greater independence for disabled people, where brain activity is present but muscular activity may not be, has resulted in significant improvements in technologies relating to brain wave recording and analysis.

Current mechanisms for controlling devices include a joystick, which is only useful where the person has predictable movement control of their hands, and multi-channel electroencephalogram (EEG) systems that endeavour to derive information from the firing of specific neurons.

These solutions either are not capable for use by many disabled people, or require multi-channel inputs to distinguish between various intents of the user, which can be time-consuming and complex to process.

It would be desirable to overcome or alleviate at least one of the above-described problems, or at least to provide a useful alternative.

SUMMARY

Disclosed is a method for identifying an event, the method comprising:
  receiving first data comprising concurrently recorded electroencephalogram (EEG) and electromyogram (EMG) signals from a user, the EEG and EMG signals resulting from movements by the user;
  forming first segments from the first data;
  computing at least one statistical property of each first segment and forming a histogram to determine thresholds of the statistical property based on:
  the number of trials; and
  a number of segments in which the at least one statistical property indicated the event based on the at least one statistical property and the thresholds;
  receiving second data comprising further EEG and EMG signals recorded from the user;
  forming second segments from the second data and computing the statistical property for each second segment; and
  processing the second segments using the histogram to determine whether the event has occurred.

Processing the second segments using the histogram to determine whether the event has occurred may comprise determining whether the event has occurred based on a number of second segments in which the at least one statistical property exceeds a first threshold defined by the at least one statistical property (indicative second segments). The event may be determined to have occurred if the number of indicative second segments exceeds a second threshold.

The at least one statistical property may include a peak-to-trough value. The at least one statistical property may include a peak-to-trough value for each channel on which the EEG and EMG values are recorded.

Each first segment is a sample may be formed by sliding window sampling the first data.

Upon determining the event has occurred, the method may then:
  compare the second data to a classification model to determine a user movement represented by the second data; and
  determine a control signal for controlling an autonomous vehicle, based on the user movement.
  disclosed herein is a method for classifying signals for movement control of an autonomous vehicle, comprising:
  receiving first data comprising concurrently recorded electroencephalogram (EEG) and electromyogram (EMG) signals from a user, the EEG and EMG signals resulting from movements by the user;
  training a classification model based on the recorded signals, wherein the classification model comprises one or more data segments, by:
  forming first segments from the first data;
  computing at least one statistical property of each first segment and forming a histogram to determine thresholds of the statistical property based on:
  the number of trials; and
  a number of segments in which the at least one statistical property indicated the event based on the at least one statistical property and the thresholds;
  receiving second data comprising further EEG and EMG signals recorded from the user;
  forming second segments from the second data and computing the statistical property for each second segment; and
  processing the second segments using the histogram to determine whether the event has occurred;
  upon determining the event has occurred, comparing the second data to the classification model by:
  extracting a segment of the second data; and
  determining one or more similarity measures between the extracted segment and data segments of the classification model, to determine a user movement represented by the second data; and
  determining a control signal for controlling the autonomous vehicle, based on the user movement.

Determining a control signal for controlling the autonomous vehicle may comprise identifying a two-dimensional movement of the autonomous vehicle corresponding to the user movement.

Receiving the first data may comprise recording EEG and EMG from the forehead of the user using one or more 2-channel sensors. Receiving the second data may comprise recording EEG and EMG from the forehead of the user using one or more 2-channel sensors.

The one or more similarity measures may include Euclidean Distance or Dynamic Time Warping Distance between the segment extracted from the second data and each data segment of the classification model.

The disclosure further provides an apparatus for classifying signals for movement control of an autonomous vehicle, comprising:
  at least one electroencephalogram (EEG) sensor for positioning on a forehead of a user;
  at least one electromyogram (EMG) sensor for positioning on the forehead of the user;
  memory; and
  at least one processor, the memory comprising instructions that, when executed by the at least one processor, cause the apparatus to:
  receive, at the at least one processor, first data from the at least one EEG sensor and at least one EMG sensor, the first data comprising concurrently recorded electroencephalogram (EEG) and electromyogram (EMG) signals from a user, the EEG and EMG signals resulting from movements by the user;
  train, using the at least one processor, a classification model based on the recorded signals, wherein the classification model comprises one or more data segments, by:
  forming first segments from the first data;
  computing at least one statistical property of each first segment and forming a histogram to determine thresholds of the statistical property based on:
  the number of trials; and
  a number of segments in which the at least one statistical property indicated the event based on the at least one statistical property and the thresholds;
  receive, at the at least one processor, second data from the at least one EEG sensor and at least one EMG sensor, the second data comprising further EEG and EMG signals recorded from the user;
  forming second segments from the second data and computing the statistical property for each second segment; and
  processing the second segments using the histogram to determine whether the event has occurred;
  upon determining the event has occurred, compare, using the at least one processor, the second data to the classification model by:
  extracting a segment of the second data; and
  determining one or more similarity measures between the extracted segment and data segments of the classification model,
  to determine a user movement represented by the second data; and
  determine, using the at least one processor, a control signal for controlling the autonomous vehicle, based on the user movement.

Determining a control signal for controlling the autonomous vehicle may be performed by identifying a two-dimensional movement of the autonomous vehicle corresponding to the user movement.

Each sensor of the at least one EEG sensor may be a 2-channel sensor. Each sensor of the at least one EMG sensor may be a 2-channel sensor.

Before receiving first data from at least one EEG sensor and at least one EMG sensor, the at least one processor may cause the apparatus to:
  receive, at the at least one processor, event detection data from the at least one EEG sensor and at least one EMG sensor, the event detection data comprising concurrently recorded electroencephalogram (EEG) and electromyogram (EMG) signals from a user, the EEG and EMG signals resulting from movements by the user;
  form, using the at least one processor, first segments from the first data;
  compute, using the at least one processor, at least one statistical property of each first segment and forming a histogram to determine thresholds of the statistical property based on:
  the number of trials; and
  a number of segments in which the at least one statistical property indicated the event based on the at least one statistical property and the thresholds;
  receive, at the at least one processor, the second data;
  form, using the at least one processor, second segments from the second data and computing the statistical property for each second segment; and
  process, using the at least one processor, the second segments using the histogram to determine whether the event has occurred.

The event detection data may be the first data, or the EMG data from the first data.

Also disclosed herein is an apparatus for identifying an event, the apparatus comprising:
  at least one electroencephalogram (EEG) sensor for positioning on a forehead of a user;
  at least one electromyogram (EMG) sensor for positioning on the forehead of the user;
  memory; and
  at least one processor, the memory comprising instructions that, when executed by the at least one processor, cause the apparatus to:
  receive, at the at least one processor, event detection data from the at least one EEG sensor and at least one EMG sensor, the event detection data comprising concurrently recorded electroencephalogram (EEG) and electromyogram (EMG) signals from a user, the EEG and EMG signals resulting from movements by the user;
  form, using the at least one processor, first segments from the event detection data;
  compute, using the at least one processor, at least one statistical property of each first segment and forming a histogram to determine thresholds of the statistical property based on:
  the number of trials; and
  a number of segments in which the at least one statistical property indicated the event based on the at least one statistical property and the thresholds;
  receive, at the at least one processor, the further event data from the at least one EEG sensor and at least one EMG sensor, the further event data comprising further EEG and EMG signals recorded from the user;
  form, using the at least one processor, second segments from the further event data and computing the statistical property for each second segment; and
  process, using the at least one processor, the second segments using the histogram to determine whether the event has occurred.

The instructions, when executed by the at least one processor, may further cause the apparatus to:
  compare the further event data to a classification model to determine a user movement represented by the further event data; and
  determine a control signal for controlling an autonomous vehicle, based on the user movement,
  upon determining the event has occurred. This may be performed in accordance with the method described above, for classifying signals for movement control of an autonomous vehicle. In this case, the event detection data may be the first data, or may comprise the EMG data from the first data. Similarly, the further event data may be the second data or the second data may be a subset of the further event data, that subset being the portion or segments of the further event data that contain the detected or determined event.

BRIEF DESCRIPTION OF THE DRAWINGS

Embodiments of the present invention will now be described, by way of non-limiting example, by reference to the drawings, in which.

DETAILED DESCRIPTION

Disclosed herein are multi-class EEG/EMG processing and classification systems. Some of the disclosed systems use a forehead EEG headband to detect EEG/EMG changes associated with 5 different actions. The output of the EEG and EMG classification system can then be used to control 2D movements of a drone (or other vehicle—e.g., wheelchair) to move up, move down, strafe left, strafe right and hover.

Figure 1:
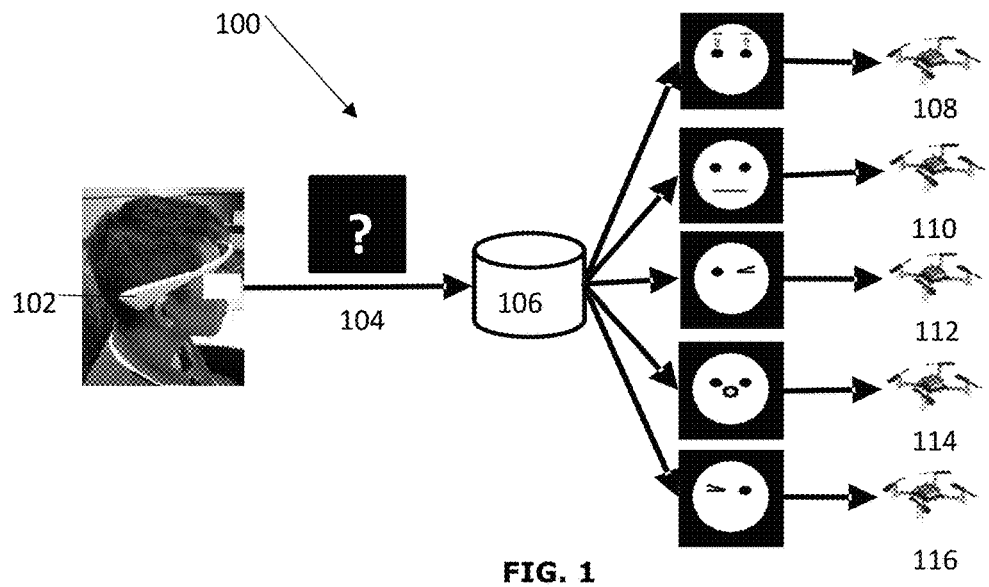
FIG. 1 is a simplified illustration of the capture, storage, and use of EEG and EMG signals in accordance with an embodiment of the invention.

An embodiment of the process disclosed herein is illustrated in a simplified flow 100, in FIG. 1. EEG and EMG signals are captured by a headband 102. The EEG and EMG in the present case relate to voluntary user movements, particularly facial expressions, that are sent for comparison 104 with a training model/trained classification model 106. The result of that comparison is that the newly recorded EEG and EMG are classified, using a list of predicted facial expression control signals, as indicating one of presently five control signals for an autonomous vehicle—presently a drone. The control signals are:

move up (108)—corresponding to raising of the eyebrows;

hover (110)—corresponding to a flat expression or no expression (i.e. default);

move right (112)—corresponding to a wink of the right eye;

move down (114)—corresponding to wiggling the nose; and move left (116)—corresponding to a wink of the left eye.

Figure 2:
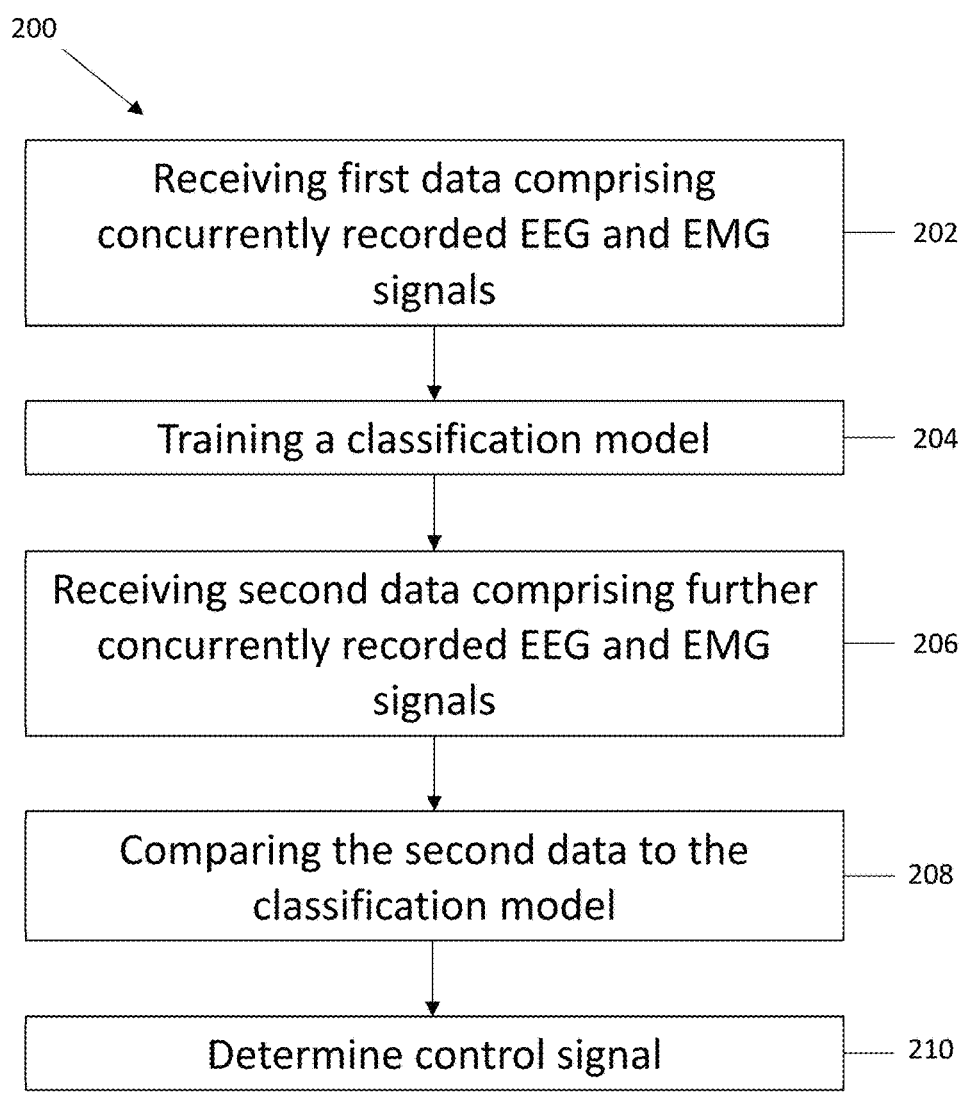
FIG. 2 illustrates a method for classifying signals for control of an autonomous vehicle.

A method 200 for classifying signals for movement control of an autonomous vehicle, is shown in FIG. 2. Broadly, the method 200 comprises:

Step 202: receiving first data comprising concurrently recorded electroencephalogram (EEG) and electromyogram (EMG) signals from a user;

Step 204: training a classification model;

Step 206: receiving second data comprising further EEG and EMG signals recorded from the user;

Step 208: comparing the second data to the classification model; and

Step 210: determining a control signal based on the user movement determined at step 208.

Steps 202 and 204 relate to a training process using EEG and EMG resulting from movements by the user. To use the methods described herein, the subject or user may therefore be required to go through a training process where they are required to perform a series of different voluntary facial expressions after the onset of a cue (synchronized training). The data collected during the training process is used to build a training model.

Figure 15:
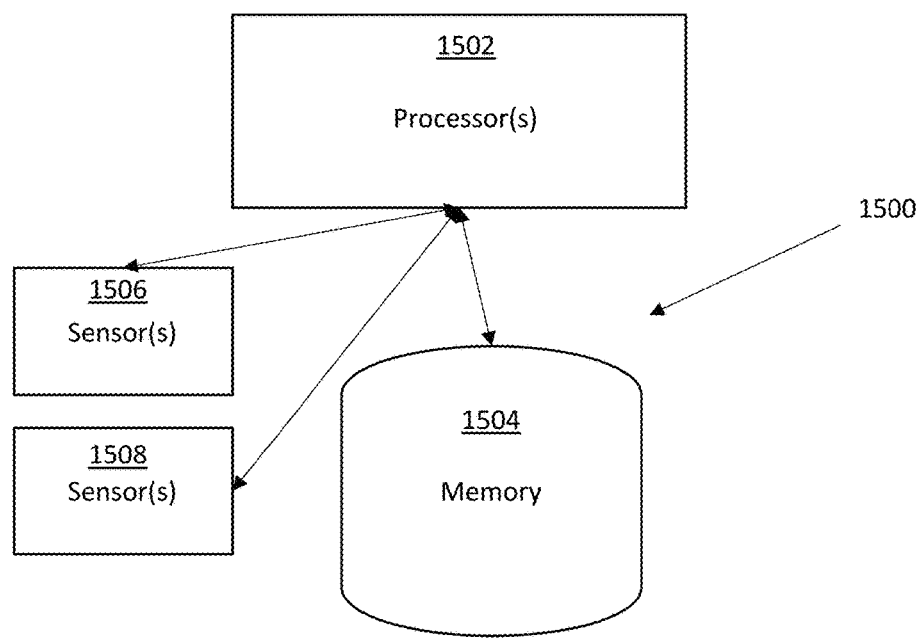
FIG. 15 illustrates a system for performing the methods of FIGS. 2, 4, 5, 6, 12 and 13.

The system, described with reference to FIG. 15, is trained on EEG/EMG data (i.e. the first data mentioned in step 202) collected during a single trial data collection process shown in FIG. 3. The EEG/EMG data are concurrently recorded from the forehead of the user using one or more 2-channel sensors.

The subject is tasked to perform one of 5 different voluntary facial expressions in each trial. While presently 5 facial expressions have been selected, there may be greater or fewer expressions depending on the complexity of the device and its freedom of movement, or the complexity of the movements being performed. EEG/EMG data collected during these single trials are then used to build the training model per step 204. The training model can then be used for later comparison with real-time or test data.

Figure 3:
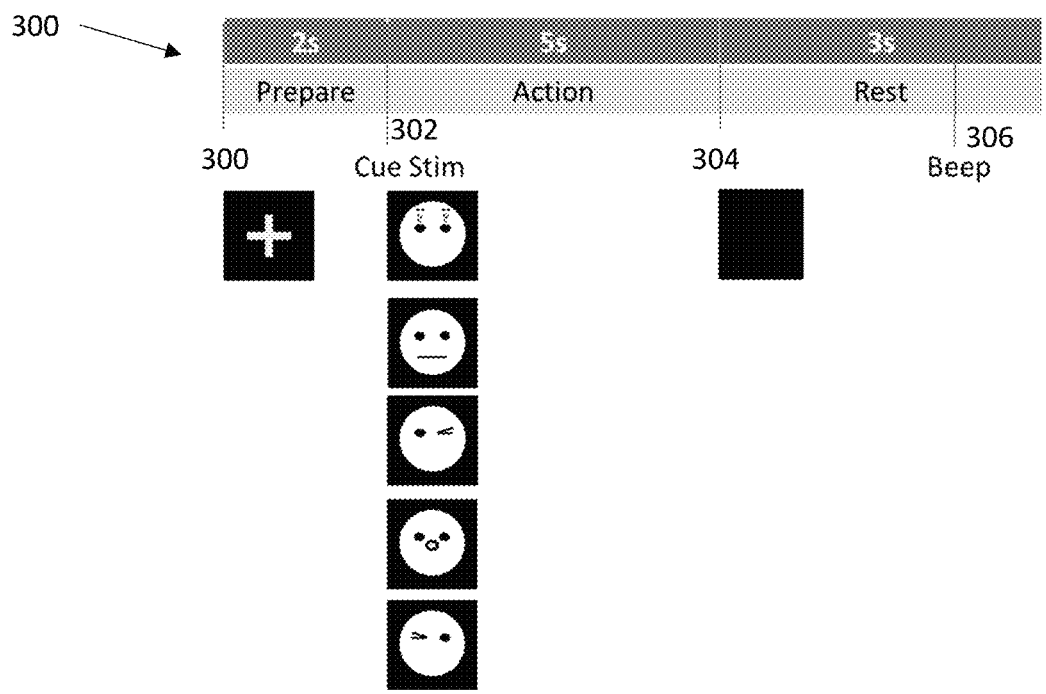
FIG. 3 shows the test sequence for obtaining EEG/EMG Test Data.

In FIG. 3, the data collection process 300 starts by visually prompting a user to prepare for performance of a facial expression—step 302. A predetermined time period later, presently 2 seconds, a stimulus cue is delivered to prompt the user to perform a particular one of the (presently) five facial expressions—step 304. The user maintains that expression over an action period, or performs it repeatedly for that period. The action period—i.e. the period over which the facial expression is to be performed or repeated—is presently 5 seconds. The system then prompts the user to cease performing the facial expression—step 306. This enables EEG and EMG data at the start and end of each action period to be synchronised with the timing of the trial, thereby enabling identification of the commencement and completion of a facial gesture.

After a rest period, presently three seconds, the system beeps to indicate completion of the trial and then next trial then starts, or starts after a predetermined time.

The trials are therefore cue-based or synchronous, and can involve any number of individual trials before sufficient data is collected to enable training of the classification model. Presently, there are 10 trials performed for each action, for a total of 50 trials lasting approximately 9 minutes.

With further reference to FIG. 2, step 206 involves receiving second data comprising further EEG and EMG signals recorded from the user. As with the first data the second data can be recorded from the forehead of the user using one or more 2-channel sensors.

The second data can be captured during testing or later use. This second data is then compared to the classification model—step 208—and a control signal is then determined 210 based on the outcome of the comparison performed at step 208.

Therefore, during testing or operation of a drone or other autonomous vehicle, the EEG/EMG data recorded during the subject's performance of voluntary facial expressions—step 206—are compared with the data in the training model—step 208. The system then makes a prediction on the facial expression action of the subject—step 210—and a classification output is computed, to move the drone. Step 210 may also include outputting the determined controlled signal.

During collection of the second data per step 206, the system can either operate in a synchronous (cue-based single trials—see FIG. 4) or asynchronous (cue-less—see FIG. 5) mode. In a synchronous system, the subject is given a cue at regular intervals to perform voluntary facial expressions, which move the drone. In an asynchronous system, the subject is not required to wait for the regular cue.

In the current system, the first data (i.e. training data) and second data (i.e. testing or real-time use data) are segmented. The model is formed using the segmented first data. A segment of the second data is compared against each segment in the training model and at least one similarity measure is calculated between the segment of the second data and each segment of the training model. The similarity measure may be, for example, Euclidean Distance or Dynamic Time Warping Distance between the segment extracted from the second data and each data segment of the classification model.

The classification of the data segment extracted from the second data will be based on the training data label whose distance is the closest to this extracted data segment—step 210. In this manner a data segment, being or representing a signal or part thereof, can be used for identifying a two-dimensional movement of the autonomous vehicle corresponding to the user movement—e.g., by cross-referencing the detected user movement against the list of autonomous vehicle control signals to determine which control signal corresponds with the user movement.

Figure 4:
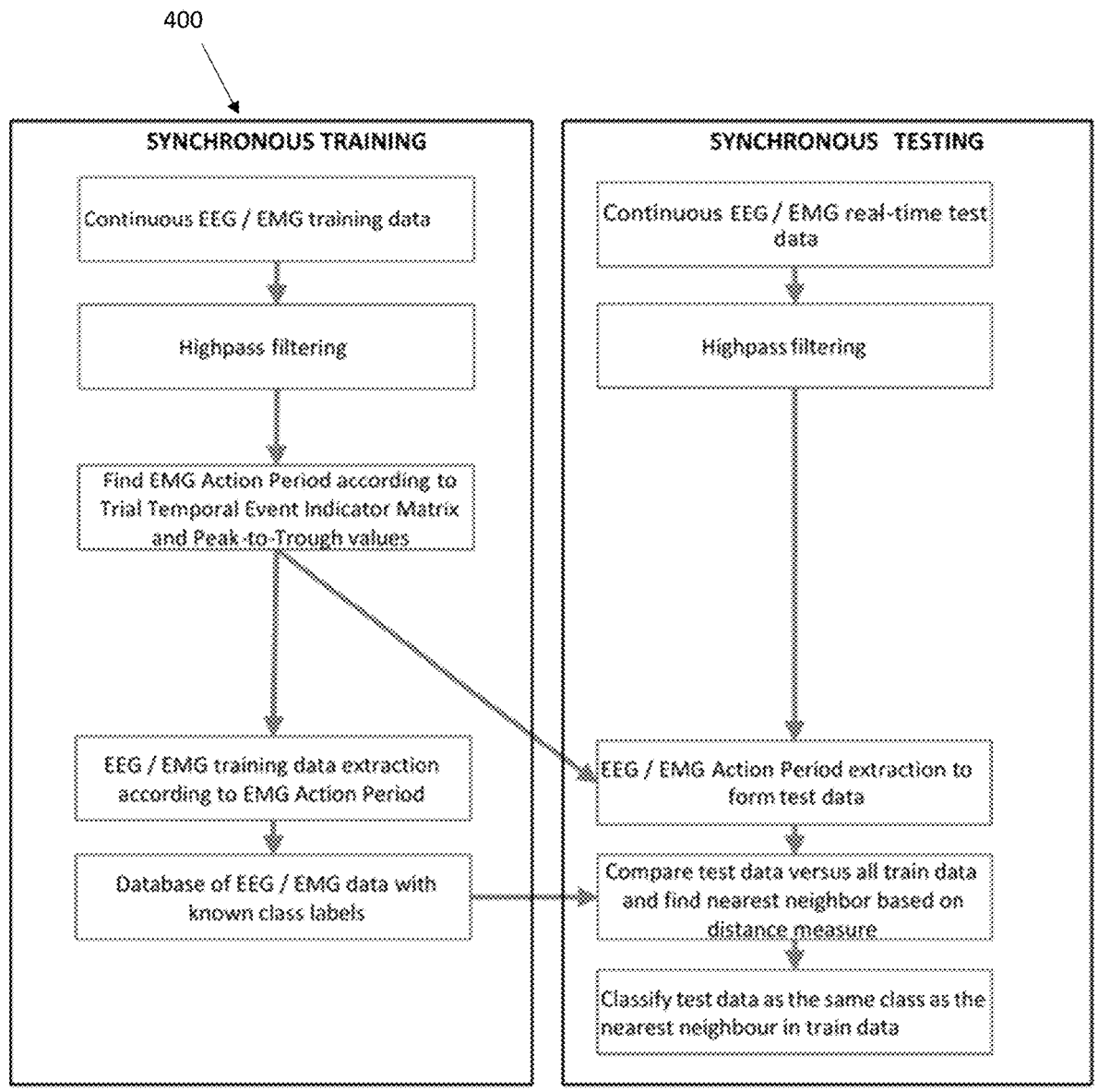
FIG. 4 provides a flowchart for the training process and subsequent use of the present method for the classification of synchronously obtained test or real-world data.

As mentioned above, collection of the second data or EEG/EMG Test Data can be synchronous or asynchronous. FIG. 4 illustrates synchronous classification. In particular, the process 400 of FIG. 4 involves the continuous and/or concurrent recording of EEG and EMG data—first data—at step 402. To reduce noise and computation time, that data undergoes highpass filtering—step 404. Step 402 has been discussed with reference to step 202 of FIG. 2, and highpass filtering will be understood by the skilled person.

After filtering (if any) the EMG Action Period is identified using a trial temporal event indicator matrix and peak-to-trough values—step 406. This step is discussed further, with reference to FIG. 6.

After the action period is identified, the relevant data—i.e. that which represents the action period, or period over which the cued facial expression was being performed or repeated—is extracted (step 408) and used to form the classification model (step 410). Presently, the classification model comprises a database of labelled EEG/EMG data—i.e. known class labels or user expressions.

During synchronous testing or real-time use, EEG and EMG data (EEG/EMG Test Data) are again continuously and/or concurrently acquired—step 412. These data again undergo highpass filtering—step 414. The EMG action period identified at step 406 is then used to locate and extract EEG and EMG data occurring during the action period (EEG/EMG Action Period Data), from the EEG/EMG Test Data—step 416.

The EEG and EMG data occurring over the action period is that which can be analysed to determine which facial expression has occurred or, in some cases, whether a facial expression was performed. The EEG/EMG Action Period Data are then compared against all the training data segments to find its nearest neighbour based on a distance measure—e.g., Euclidean Distance or Dynamic Time Warping Distance—step 418.

The EEG/EMG Action Period Data is then assumed to represent the same gesture as that performed during acquisition of the data segment of the training data that is closest to the EEG/EMG Action Period Data, by distance—step 420.

Figure 5:
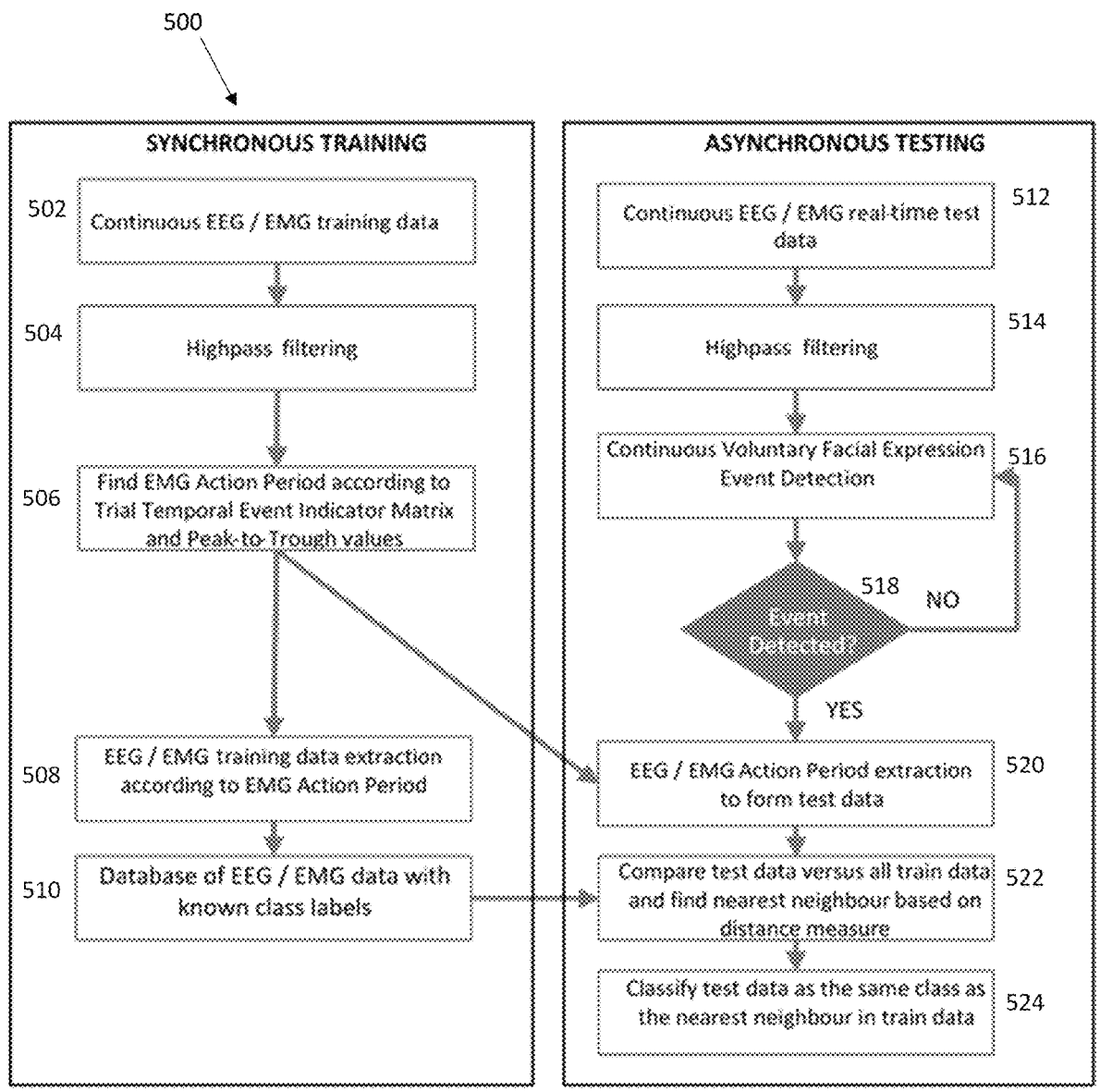
FIG. 5 provides a flowchart for the training process and subsequent use of the present method for the classification of asynchronously obtained test or real-world data.

FIG. 5 illustrates an asynchronous classification process 500. Step 502 to 514 are substantially the same as respective steps 402 to 414 of FIG. 4. The only difference is step 414 may occur either continuously or commence a predetermined time before a cue, whereas step 514 will generally occur continuously since it is unknown when the next facial expression will be voluntarily performed by the user.

Step 516 involves continuously monitoring EEG/EMG Test Data for a voluntary facial expression. Continuous voluntary facial expression detection is discussed with reference to FIG. 13.

If, at step 518, no event is detected then step 516 is repeated. If, at step 518, an event is detected steps 520, 522 and 524 are performed in sequence. These steps are substantially the same as steps 416, 418 and 520 respectively.

As mentioned above, in order to perform the comparison step the EEG/EMG data representing an event must be extracted from the first (training) data and second (test) data. To extract that data the EMG Action Period must be identified and the data acquired over that period extracted. Steps 406 and 506 involve the identification of the EMG Action Period and calculation of subject-specific peak-to-trough values.

Figure 6:
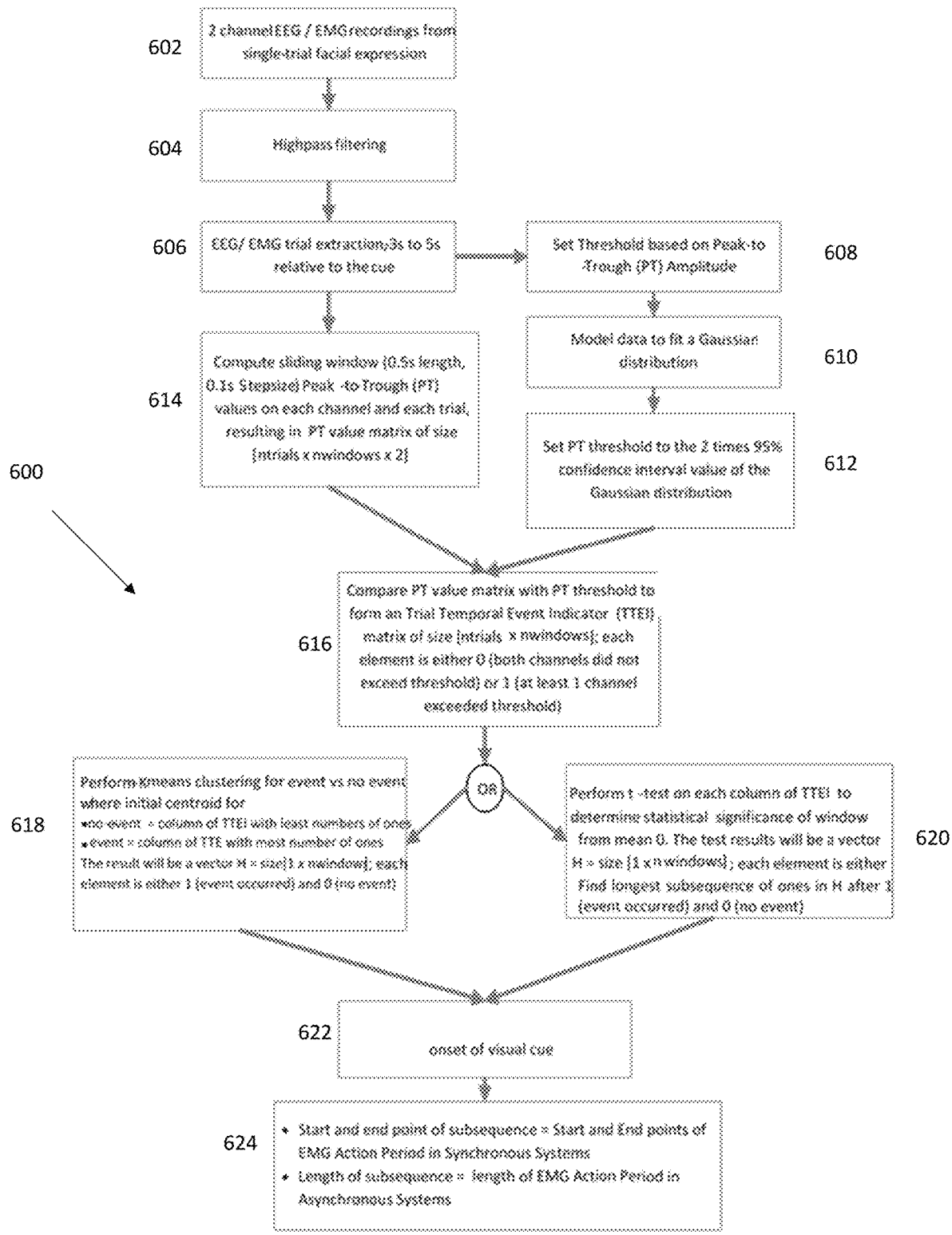
FIG. 6 provides a flowchart for the subject-specific peak-to-trough amplitude threshold computation for voluntary facial expression event detection, and identification of EMG Action Period.

FIG. 6 provides a flowchart 600 for the subject-specific peak-to-trough amplitude threshold computation for voluntary facial expression event detection during capture of training data (event detection data), and identification of EMG Action Period. Step 602 involves capturing EMG (event detection) data using a 2-channel sensor. The EMG data may result from single-trial facial expression capture. Again, highpass filtering or other filtering may be performed—step 604. The filtering may be at 0.05 Hz, 0.1 Hz, 0.2 Hz, or any other threshold.

The EEG/EMG data for the trial is then extracted from 3 seconds (or any other desired length of time) before the cue commenced per step 302 of FIG. 3, to 5 seconds (or any other desired length of time) after the cue completed per step 304 of FIG. 3. This extracted data is then processed in two ways. Firstly, a threshold is set based on peak-to-trough (PT) amplitude—step 608. This enables the data to be modelled to fit a Gaussian distribution—step 610—to enable isolation of the facial expression event.

Figure 7:
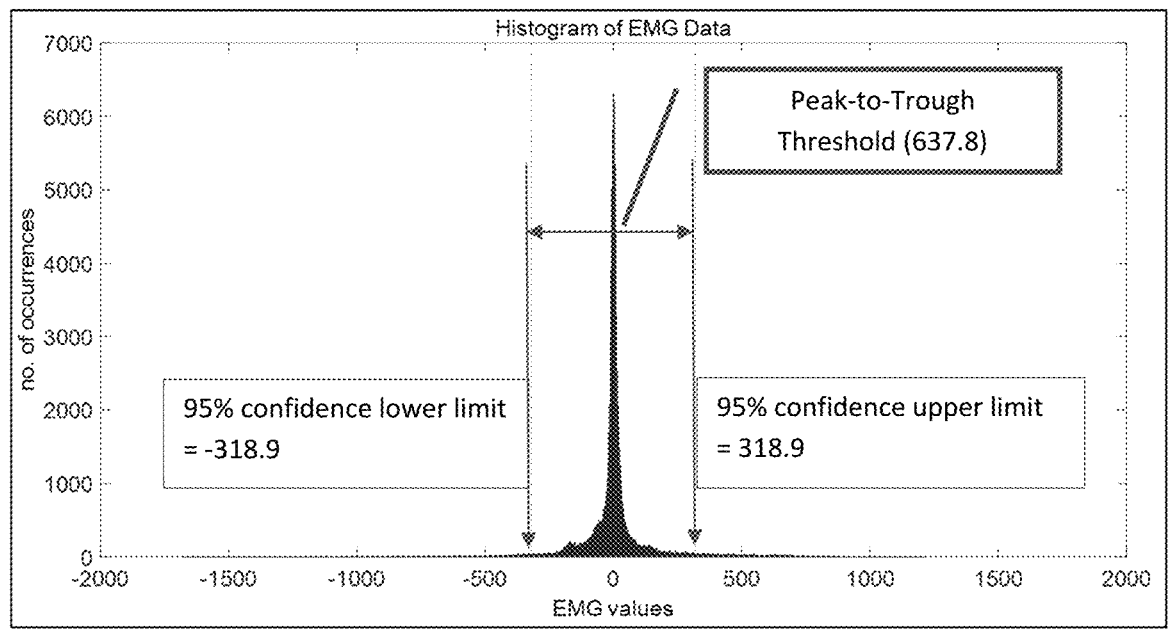
FIGS. 7 and 8 show EMG data from two subjects and determination of the PT threshold.
Figure 8:
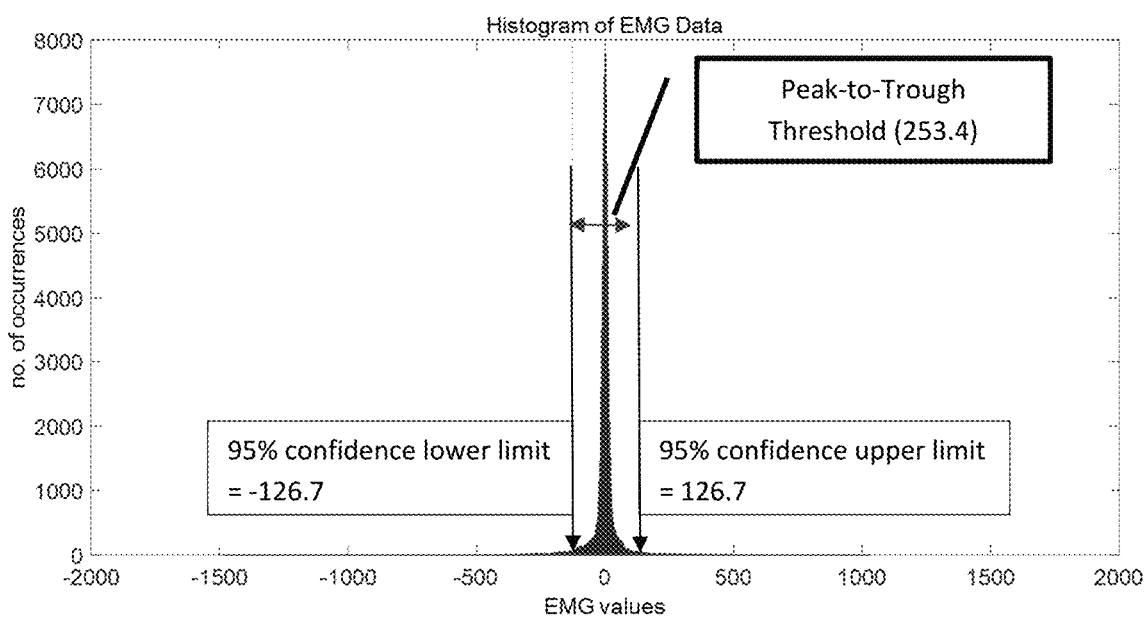

The 95% confidence interval is computed around against the Gaussian distribution—e.g., around the data spike signifying commencement of the facial expression. This is illustrated in FIGS. 7 and 8, which show the EMG data for two different subjects, illustrating the variation in response between individuals and, similarly, the variation in PT threshold. For example, the PT threshold is 637.8 and 253.4 in FIG. 7 and FIG. 8 respectively. The PT threshold is then set to either the upper limit of the 95% confidence interval—the lower limit of the 95% confidence interval, or 2 times the upper limit of the 95% confidence interval. Notably, since the response of the user is unique to the user, the PT threshold will be user-specific.

Figure 9:
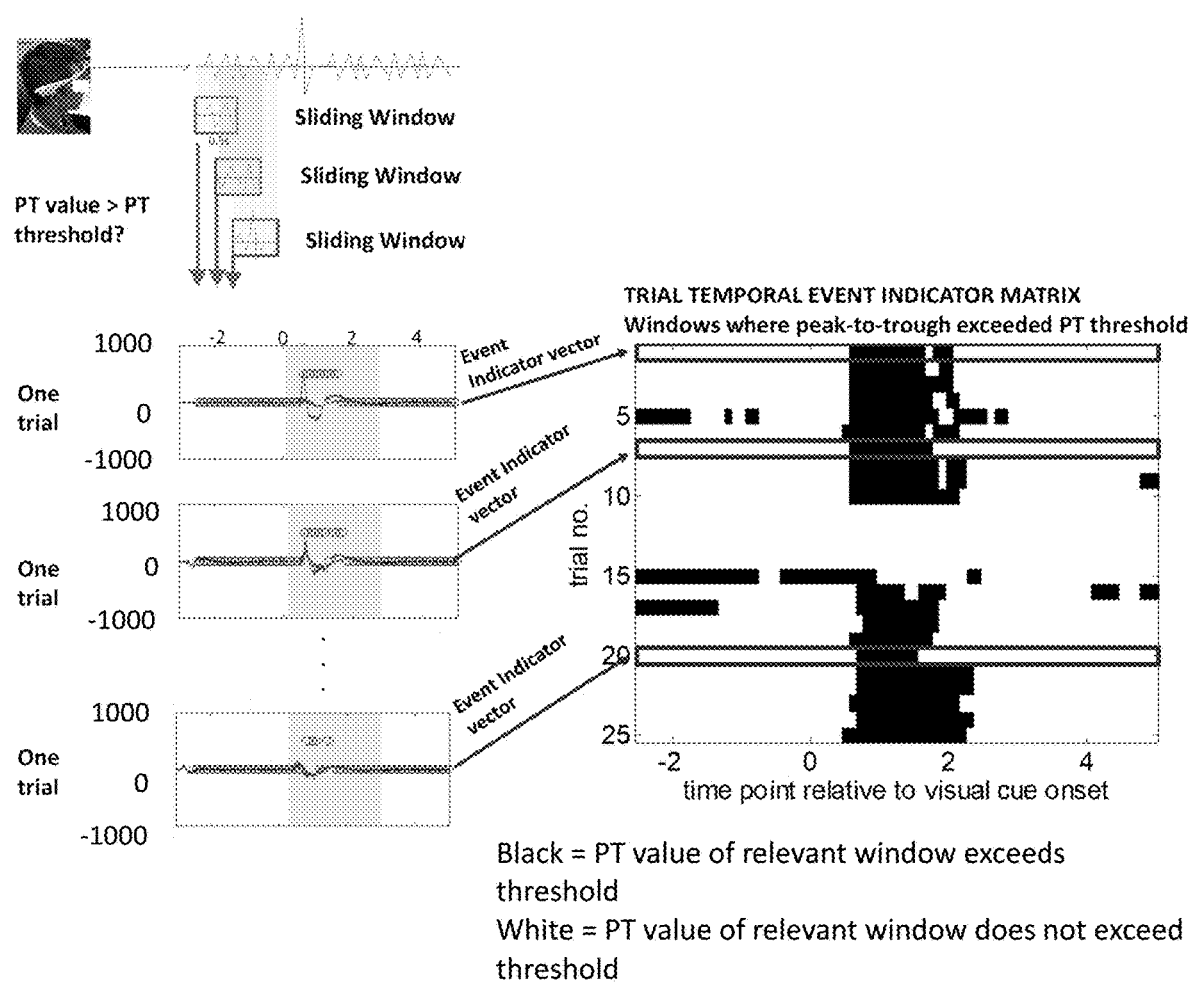
FIG. 9 is a pictorial flowchart for producing a temporal time indicator matrix.

The second way the data extracted at step 606 is used is in computing the EMG Action Period after determining the PT threshold. To do this, PT value matrix is produced. Producing the PT value matrix—per the pictorial flowchart of FIG. 9—involves applying a sliding window on the continuous EEG/EMG data. The sliding window may be 0.5 s long, with step size of 0.1 s, or any other desired length and step size. The peak-to-trough (PT) value is computed for each window. For each window, the PT value is compared against the PT threshold to form a Temporal Event Indicator vector of size [1×nWindows]—step 616. The vector comprises 1s and 0s as shown in FIG. 9—the circles in the shaded region of each trial indicate segments where the PT threshold was exceeded (above the line) and was not exceeded (on the line). The indicator for the relevant position in the vector is a 1 if the PT value is greater than or equal to the PT threshold indicator for that window, and is a 0 if the PT value is less than the PT threshold.

A Trial Temporal Event Indicator (TTIE) Matrix is then calculated. This is achieved by the row-wise concatenation of the indicator vectors for all of the trials. The size of the TTIE Matrix is therefore [nTrials×nWindows]. Each column of the TTIE therefore represents a time window of the EMG (event detection) data sampled using the sliding window.

Figure 10:
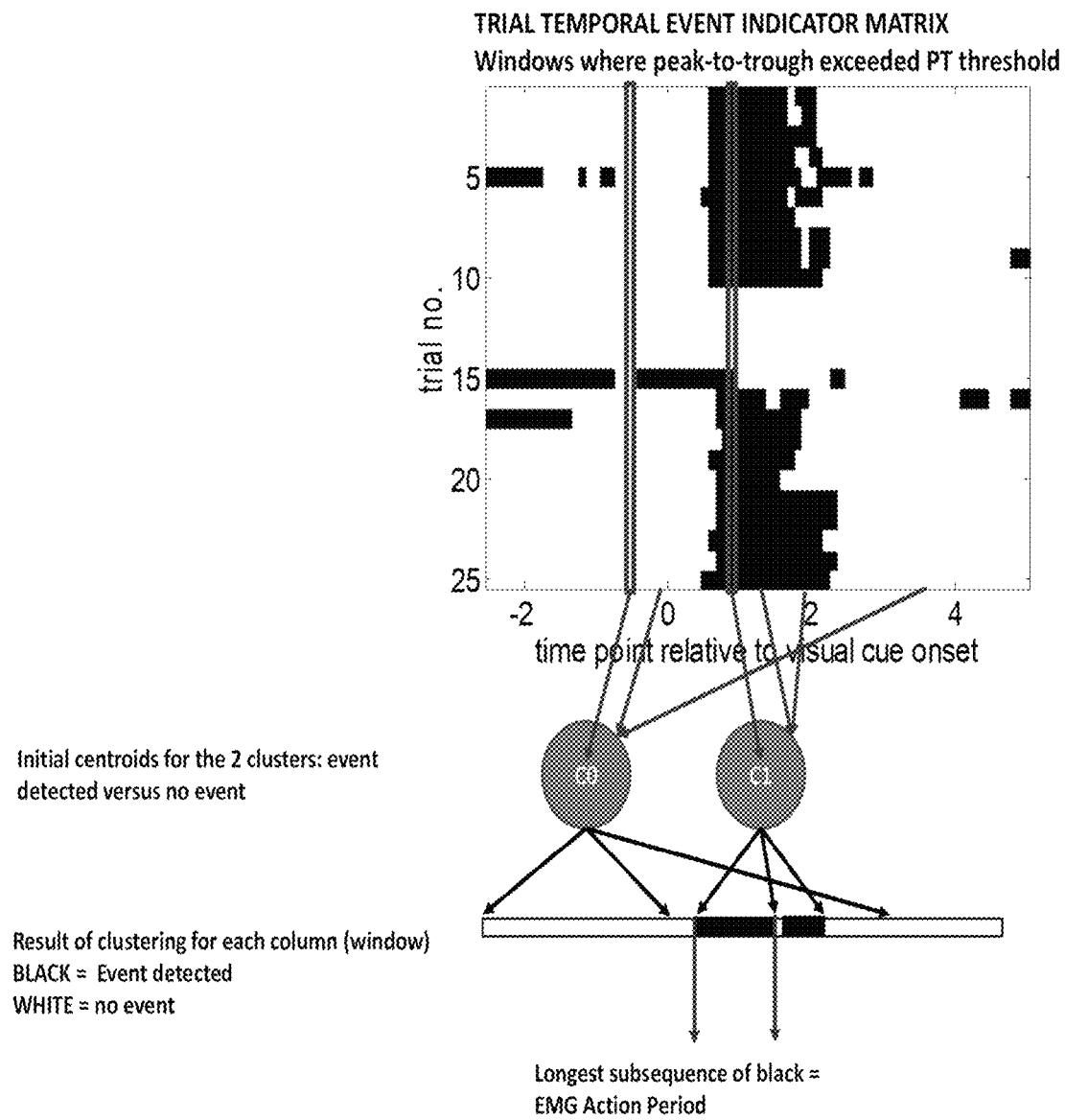
FIG. 10 illustrates distinguishing between windows with an event detected versus windows with no event detected, using a similarity measure.
Figure 11:
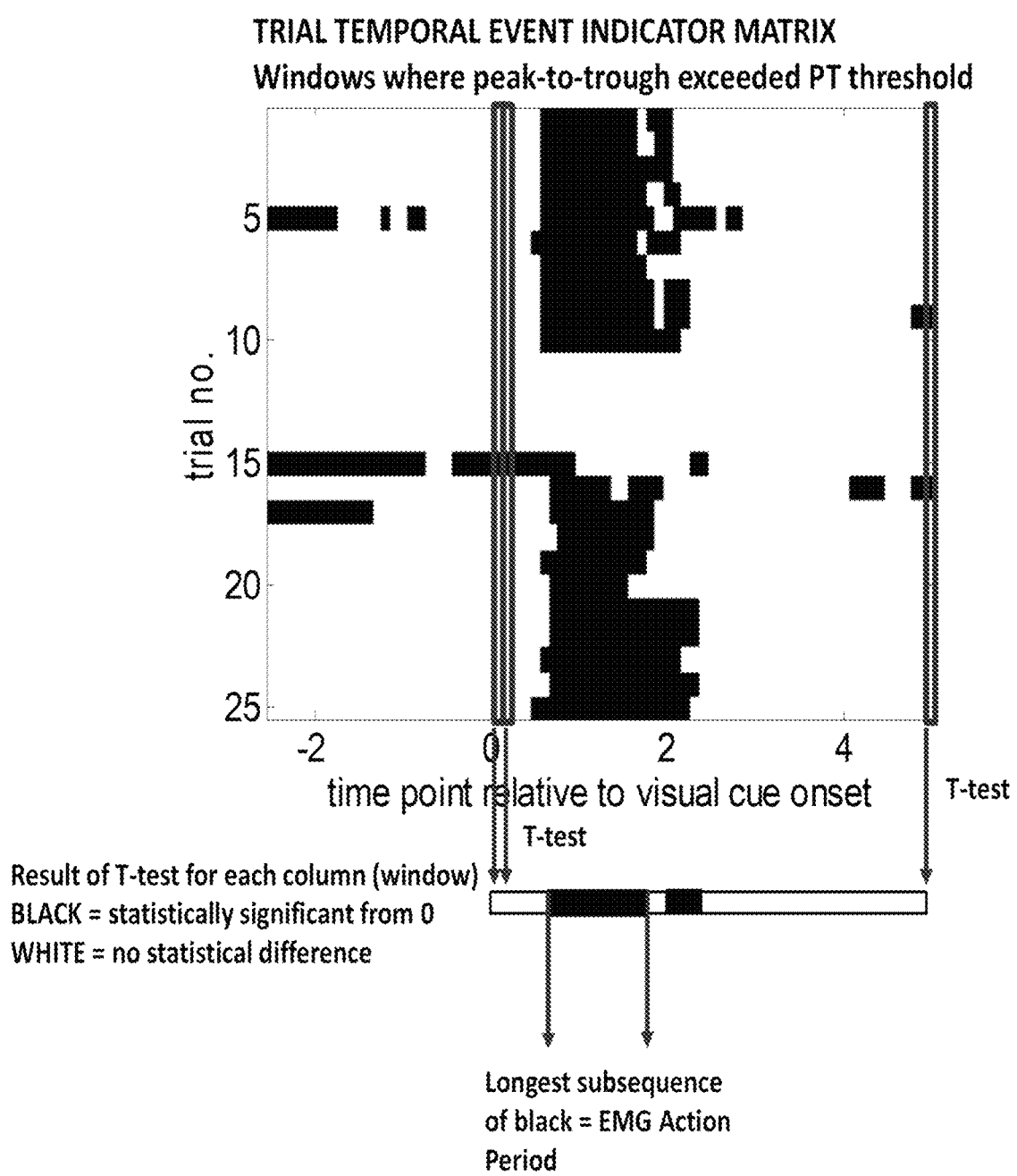
FIG. 11 illustrates distinguishing between windows with an event detected versus windows with no event detected, using statistical tests.

The time windows of the TTIE can then be analysed to determine the time windows that represent events, and those that do not. There are 2 ways to identify the time windows that have events detected versus no events detected. Firstly, as shown in FIG. 10 similarity measures can be used to determine which windows have events and which do not have events. As an example, K-Means Clustering could be employed—step 618. The initial centroids would also be preset: for example, the initial centroid for event detected can be the column of TTIE which has the most number of 1s, and initial centroid for no event can be the column of TTIE which has the least number of 1s. Alternatively, as shown in FIG. 11 a statistical test may be performed—step 620. For example, a t-test may be performed on each column of the TTIE Matrix to determine whether that particular time window is statistically significant or distinct from zero.

The result of both analyses performed as shown in FIGS. 10 and 11 is a vector H of size [1×nWindows]. Vector H indicates either 1 (event occurred) or 0 (no event). From the results or values in H, the longest subsequence of ones must be found—step 622. In general, a condition will be that the longest subsequence must be after the onset of the visual cue. Since the data on which vector H is created is training data, we know that the voluntary facial expression took place after the presentation of the visual cue.

Per step 624: the EMG Action Period for training data in synchronous mode is then set as the period between the start and end points of the longest subsequence for training data.

In addition, the length of the longest subsequence (i.e. the length of the EMG Action Period) will form the length of EEG/EMG extracted after the onset of an event detection in asynchronous mode.

Figure 12:
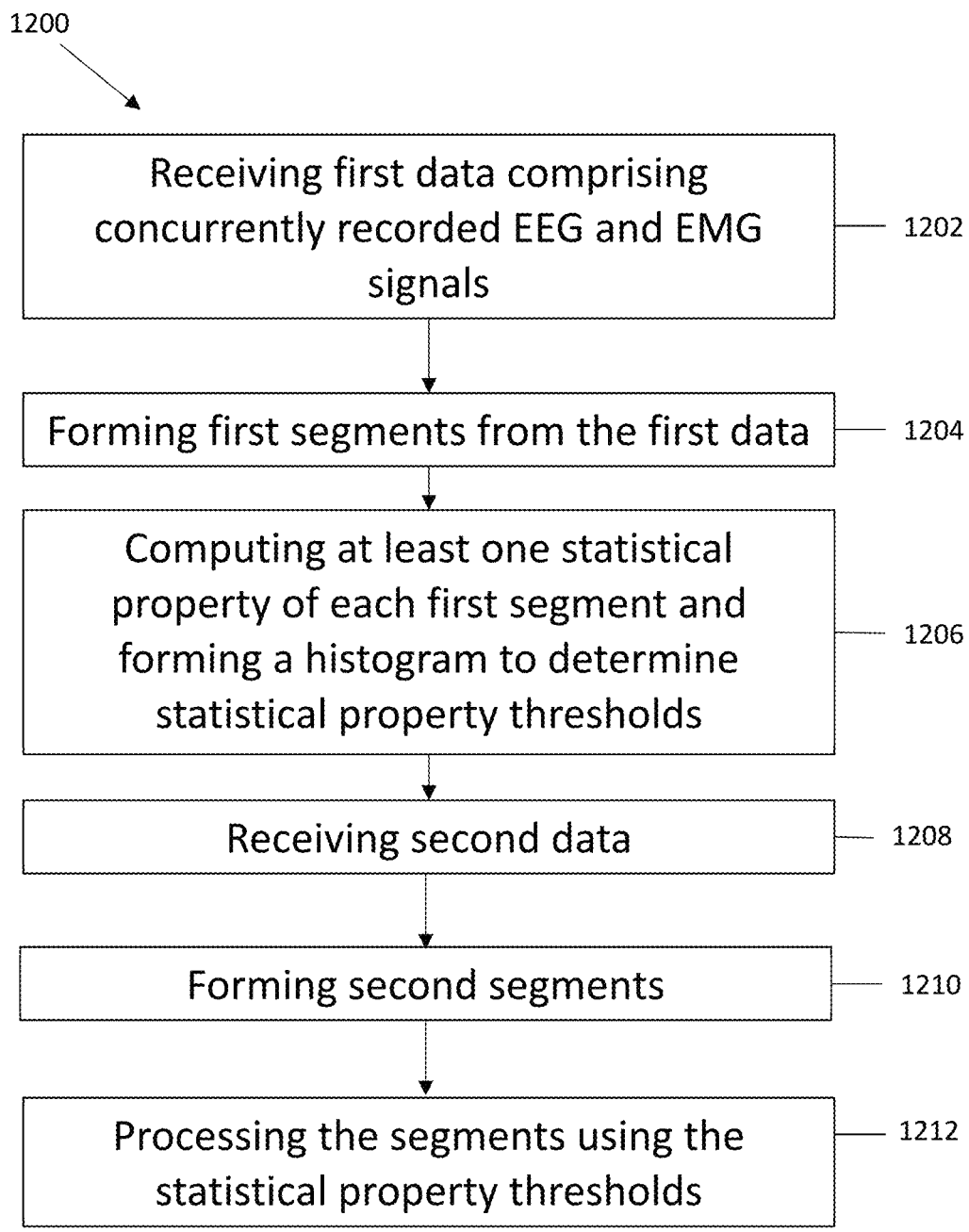
FIG. 12 is an embodiment of a method for identifying an event.

FIG. 12 illustrates a method 1200 for identifying an event or detecting the onset of an event. The method 1200 broadly comprises:

Step 1202: receiving event detection data—this data may be the first (or second) data described with reference to FIG. 2, may be the EMG data from the first (or second) data, or may be a different set of data;

Step 1204: forming first segments from the event detection data;

Step 1206: computing at least one statistical property of each first segment and forming a histogram to determine statistical property thresholds;

Step 1208: receiving further event data—this is data that may contain a further event, and whether it does will be clarified by steps 1210 and 1212. The further event data may be the second (or first) data described with reference to FIG. 2, may be the EMG component of the second (or first) data, or may be a different set of data;

Step 1210: forming second segments from the further event data; and

Step 1212: processing the second segments using the statistical property thresholds.

Step 1202 is substantially the same as step 402. Step 1204 involves forming first segments in substantially the same manner in Step 606. Step 1206 involves computing at least one statistical property (e.g. peak-to-trough value) of each first segment in substantially the same manner in Step 608, and subsequently forming the statistical property thresholds in substantially the same manner in Step 610 and Step 612. Step 1208 involves receiving second data in substantially the same manner as step 206. The second data is then segmented in Step 1210. Lastly in Step 1212, the second segments are processed by calculating the statistical property for each segment and comparing against the statistical property thresholds to determine whether the event has occurred.

Figure 13:
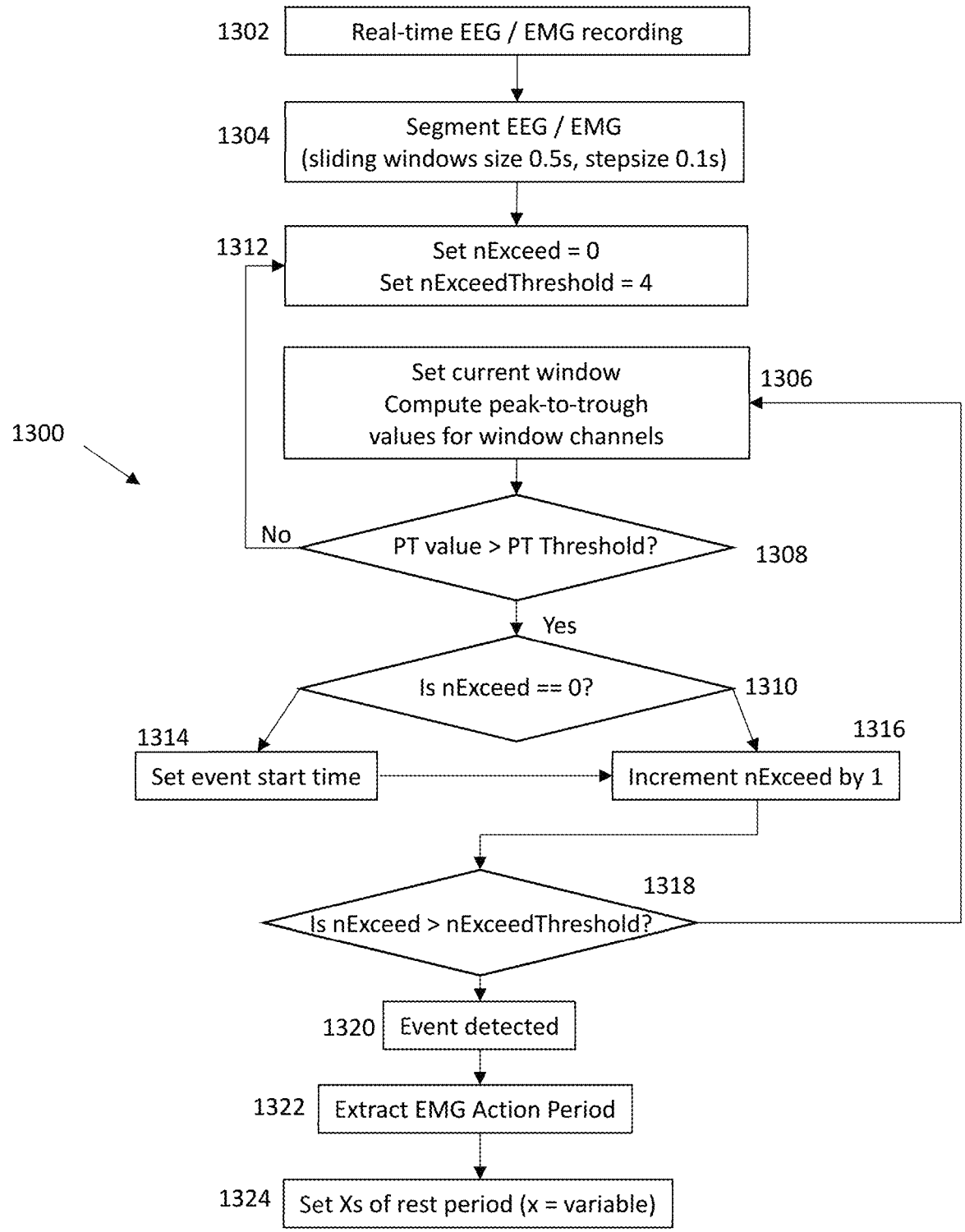
FIG. 13 is a further embodiment of a method for identifying an event.

The method 1200 can be used for asynchronous system detection of the onset of a voluntary facial expression. A flowchart illustrating the method 1200 is shown in FIG. 13 in which EEG/EMG data is recorded as discussed above—step 1302. The EEG/EMG data is then sampled. Sampling is made by applying a sliding window of 0.5 s with a step size of 0.1 s on the continuous data—step 1304. For each sliding window, the peak-to-trough (PT) value for that window is computed—step 1306—and compared against the PT threshold—step 1308. If the PT value of the window or segment is greater than or equal to the PT threshold then an increment of 1 is applied to the number of consecutive windows that exceed the threshold (N)—step 1310. If, prior to this window, N=0 then the event start time is set to the start of this window. N is set to 0 by default. If the PT value is less than the PT threshold, then N is reset to 0—step 1312.

At step 1318, if the number of consecutive windows which exceed the threshold is less than a predetermined number—e.g., 4—the process moves back to step 1306 and awaits computation of the next window. If N is equal to a predetermined number or threshold—e.g., N=4—an event is deemed to be detected. The event is also deemed to have started at the start of the earliest window in the sequence—step 1320. Therefore, processing the second segments using the histogram to determine whether the event has occurred comprises determining whether the event has occurred based on a number of second segments in which the at least one statistical property exceeds a first threshold defined by the at least one statistical property.

A time segment of EEG/EMG data equivalent to the length of time segment computed for the training time segment earlier (i.e. the Action Period) is extracted for processing by the classifier—step 1322. Comparing this time segment (i.e., second data or EEG/EMG Test Data) to the classification model can then determine a user movement represented by the time segment. A control signal for controlling an autonomous vehicle corresponding to the user movement indicated by the event can then be identified.

The Action Period is thus used to define the start and end points of the data to be extracted (or duration of the data to be processed) from each training data trial for training the model, and subsequently from the second data for detecting real-time events.

The control signal can then be transmitted to the autonomous vehicle to control the autonomous vehicle.

Once a classifier output has been computed, the system will have a predefined rest period before the subject is allowed to input his next command—step 1324.

Using the methods described above, a 2-sensor (i.e., 2-channel) EEG headband can achieve 2-dimensional (2D) control movements of a drone using EEG and EMG signal changes recorded concurrently. EMG is not known to be used for such control due to its high noise. Thus EMG has been typically used where neurons are known to control a particular muscular function and thus firing of those neurons indicates an attempt to perform that function—e.g., on the hand, arm or leg. Using the process discussed above, EMG signal recorded on the forehead may be used in identifying autonomous vehicle control signals.

Use of the TTIE enables automatic definition of the period of EMG action (EMG Action Period) input by the user or recorded from the user. During the training process, reaction time and performance time of the facial expressions may be different for different subjects e.g., different age groups have different reaction times and different people have different interpretations of how long the expression should last. This issue is overcome by the TTIE since it defines the EMG Action Period input based on statistical properties of the signals over all the training data collected—e.g., for the particular subject in question. The EMG Action Period is used for the training data in the training model.

Figure 14:
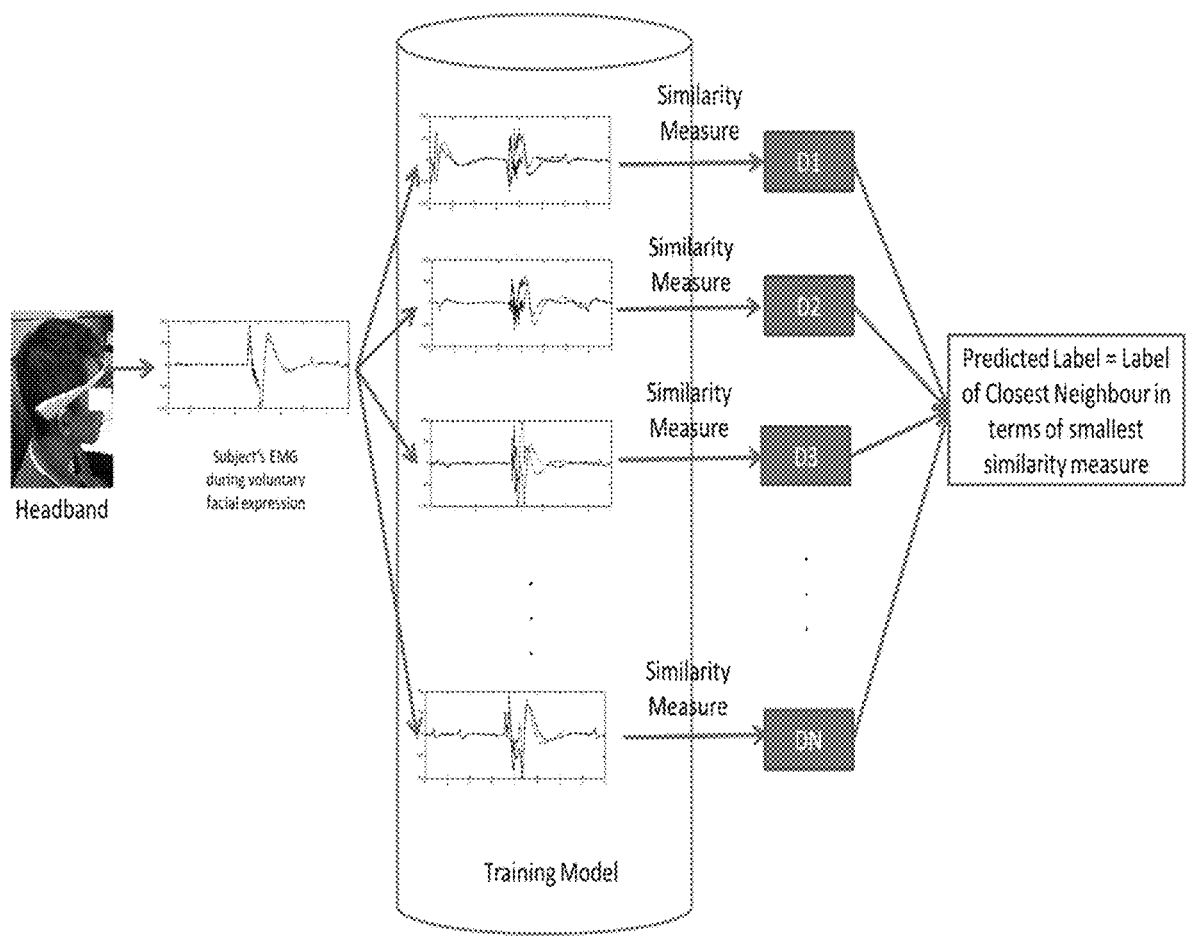
FIG. 14 is a flowchart illustrating computation of a label for new EMG data based on the smallest similarity measure of the new EMG data with training data.

In addition, as discussed above, when a new EEG/EMG trial is processed, it is compared with the existing training data in the training model. A similarity measure is computed between this new EEG/EMG trial and all the existing training data e.g., Euclidean Distance or Dynamic Time Warping Distance. This is summarized in FIG. 14. The predicted label of the new EMG trial depends on the class label of its closest neighbour as determined by the smallest distance measure, taken from potential neighbours of which the training model is composed.

FIG. 15 illustrates an apparatus 1500 for classifying signals for movement control of an autonomous vehicle, and for identifying an event (e.g., the onset of a facial expression). The apparatus 1500 includes at least one electroencephalogram (EEG) sensor (1506) for positioning on a forehead of a user, at least one electromyogram (EMG) sensor (1508) for positioning on the forehead of the user, memory (1504) and at least one processor (1502). The methods described above may be stored as instructions in the memory so that, for example, when those instructions are executed by the at least one processor they cause the apparatus to:

receive, at the at least one processor 1502, first data from the at least one EEG sensor 1506 and at least one EMG sensor 1508, the first data comprising concurrently recorded electroencephalogram (EEG) and electromyogram (EMG) signals from a user, the EEG and EMG signals resulting from movements by the user;

train, using the at least one processor 1502, a classification model based on the recorded signals, wherein the classification model comprises one or more data segments;

receive, at the at least one processor 1502, second data from the at least one EEG sensor and at least one EMG sensor, the second data comprising further EEG and EMG signals recorded from the user;

compare, using the at least one processor 1502, the second data to the classification model by:

extracting a segment of the second data; and determining one or more similarity measures between the extracted segment and data segments of the classification model, to determine a user movement represented by the second data; and determine, using the at least one processor 1502, a control signal for controlling the autonomous vehicle, based on the user movement.

The apparatus may also output that control signal to control an autonomous vehicle—e.g., drone or wheelchair.

Instead of, or in addition to, performing the train, receive (second data), compare and determine steps, the instructions may cause the apparatus to:

form, using the at least one processor, first segments from the first data (or from event detection data as the case may be);

compute, using the at least one processor, at least one statistical property of each first segment and forming a histogram to determine thresholds of the statistical property based on:

the number of trials; and a number of segments in which the at least one statistical property indicated the event based on the at least one statistical property and the thresholds;

receive, at the at least one processor, second data (or further event data as the case may be) from the at least one EEG sensor and at least one EMG sensor, the second data comprising further EEG and EMG signals recorded from the user;

form, using the at least one processor, second segments from the second data and computing the statistical property for each second segment; and process, using the at least one processor, the second segments using the histogram to determine whether the event has occurred.

The apparatus of FIG. 15 is specifically designed to be used with a 2-channel EEG headband (or sensors on the forehead) for concurrent recording of EEG and EMG data. Existing devices use only EEG since the EMG data is noisy, of may use EMG on limbs. Thus, the apparatus of FIG. 15 can facilitate easier use than previous devices, and enhanced control due to the provision of an Action Period, TTIE and similarity measure comparison of new EEG/EMG Test Data with the existing model based on EEG/EMG training data.

It will be appreciated that many further modifications and permutations of various aspects of the described embodiments are possible. Accordingly, the described aspects are intended to embrace all such alterations, modifications, and variations that fall within the spirit and scope of the appended claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method for identifying an event, the method comprising:
   receiving first data comprising concurrently recorded electroencephalogram (EEG) and electromyogram (EMG) signals from a user, the EEG and EMG signals resulting from movements by the user;
   forming first segments from the first data;
   computing at least one statistical property of each first segment and forming a histogram to determine thresholds of the statistical property based on:
      the number of trials; and
      a number of segments in which the at least one statistical property indicated the event based on the at least one statistical property and the thresholds;
   receiving second data comprising further EEG and EMG signals recorded from the user;
   forming second segments from the second data and computing the statistical property for each second segment; and
   processing the second segments using the histogram to determine whether the event has occurred.

2. The method of claim 1, wherein processing the second segments using the histogram to determine whether the event has occurred comprises determining whether the event has occurred based on a number of second segments in which the at least one statistical property exceeds a first threshold defined by the at least one statistical property (indicative second segments).

3. The method of claim 2, wherein the event is determined to have occurred if the number of indicative second segments exceeds a second threshold.

4. The method of claim 1, wherein the at least one statistical property includes a peak-to-trough value.

5. The method of claim 4, wherein the at least one statistical property includes a peak-to-trough value for each channel on which the EEG and EMG values are recorded.

6. The method of claim 1, wherein each first segment is a sample formed by sliding window sampling the first data.

7. The method of claim 1, further comprising, upon determining the event has occurred:
   comparing the second data to a classification model to determine a user movement represented by the second data; and
   determining a control signal for controlling an autonomous vehicle, based on the user movement.

8. A method for classifying signals for movement control of an autonomous vehicle, comprising:
   receiving first data comprising concurrently recorded electroencephalogram (EEG) and electromyogram (EMG) signals from a user, the EEG and EMG signals resulting from movements by the user;
   training a classification model based on the recorded signals, wherein the classification model comprises one or more data segments, by:
      forming first segments from the first data;
      computing at least one statistical property of each first segment and forming a histogram to determine thresholds of the statistical property based on:
         the number of trials; and
         a number of segments in which the at least one statistical property indicated the event based on the at least one statistical property and the thresholds;
   receiving second data comprising further EEG and EMG signals recorded from the user;
   forming second segments from the second data and computing the statistical property for each second segment; and
   processing the second segments using the histogram to determine whether the event has occurred;
   upon determining the event has occurred, comparing the second data to the classification model by:
      extracting a segment of the second data; and
      determining one or more similarity measures between the extracted segment and data segments of the classification model, to determine a user movement represented by the second data; and
   determining a control signal for controlling the autonomous vehicle, based on the user movement.

9. The method of claim 8, wherein determining a control signal for controlling the autonomous vehicle comprises identifying a two-dimensional movement of the autonomous vehicle corresponding to the user movement.

10. The method of claim 8, wherein receiving the first data comprises recording EEG and EMG from the forehead of the user using one or more 2-channel sensors.

11. The method of claim 8, wherein receiving the second data comprises recording EEG and EMG from the forehead of the user using one or more 2-channel sensors.

12. The method of claim 8, wherein the one or more similarity measures include Euclidean Distance or Dynamic Time Warping Distance between the segment extracted from the second data and each data segment of the classification model.

13. An apparatus for classifying signals for movement control of an autonomous vehicle, comprising:
   at least one electroencephalogram (EEG) sensor for positioning on a forehead of a user;
   at least one electromyogram (EMG) sensor for positioning on the forehead of the user;
   memory; and
   at least one processor, the memory comprising instructions that, when executed by the at least one processor, cause the apparatus to:
      receive, at the at least one processor, first data from the at least one EEG sensor and at least one EMG sensor, the first data comprising concurrently recorded electroencephalogram (EEG) and electromyogram (EMG) signals from a user, the EEG and EMG signals resulting from movements by the user;
      train, using the at least one processor, a classification model based on the recorded signals, wherein the classification model comprises one or more data segments, by:
         forming first segments from the first data;
         computing at least one statistical property of each first segment and forming a histogram to determine thresholds of the statistical property based on:

the number of trials; and
a number of segments in which the at least one statistical property indicated the event based on the at least one statistical property and the thresholds;
receive, at the at least one processor, second data from the at least one EEG sensor and at least one EMG sensor, the second data comprising further EEG and EMG signals recorded from the user;
forming second segments from the second data and computing the statistical property for each second segment; and
processing the second segments using the histogram to determine whether the event has occurred;
upon determining the event has occurred, compare, using the at least one processor, the second data to the classification model by:
extracting a segment of the second data; and
determining one or more similarity measures between the extracted segment and data segments of the classification model, to determine a user movement represented by the second data; and
determine, using the at least one processor, a control signal for controlling the autonomous vehicle, based on the user movement.

14. The apparatus of claim 13, wherein determining a control signal for controlling the autonomous vehicle is performed by identifying a two-dimensional movement of the autonomous vehicle corresponding to the user movement.

15. The apparatus of claim 13, wherein each sensor of the at least one EEG sensor is a 2-channel sensor.

16. The apparatus of claim 13, wherein each sensor of the at least one EMG sensor is a 2-channel sensor.

17. The apparatus of claim 13, wherein the at least one processor, before receiving second data from at least one EEG sensor and at least one EMG sensor, causes the apparatus to:
receive, at the at least one processor, event detection data from the at least one EEG sensor and at least one EMG sensor, the event detection data comprising concurrently recorded electroencephalogram (EEG) and electromyogram (EMG) signals from a user, the EEG and EMG signals resulting from movements by the user;
form, using the at least one processor, first segments from the first data;
compute, using the at least one processor, at least one statistical property of each first segment and forming a histogram to determine thresholds of the statistical property based on:
the number of trials; and
a number of segments in which the at least one statistical property indicated the event based on the at least one statistical property and the thresholds;
receive, at the at least one processor, the second data;
form, using the at least one processor, second segments from the second data and computing the statistical property for each second segment; and
process, using the at least one processor, the second segments using the histogram to determine whether the event has occurred.

18. The apparatus of claim 17, wherein the at least one statistical property includes a peak-to-trough value.

19. The method of claim 18, wherein the at least one statistical property includes a peak-to-trough value for each channel on which the EEG and EMG values are recorded.

20. The method of claim 17, wherein each first segment is a sample formed by sliding window sampling the event detection data.

* * * * *